United States Patent [19]

Kishimoto et al.

[11] Patent Number: 4,791,461
[45] Date of Patent: Dec. 13, 1988

[54] PORTABLE ANALYZER

[75] Inventors: Shinichi Kishimoto, Kumiyama; Kenichi Iwase, Joyo; Toshio Miki, Kyoto; Teiji Tanaka, Joyo, all of Japan

[73] Assignee: Syntex (U.S.A.) Inc., Palo Alto, Calif.

[21] Appl. No.: 894,176

[22] Filed: Oct. 6, 1986

Related U.S. Application Data

[63] Continuation of Ser. No. 675,485, Nov. 27, 1984, abandoned.

[51] Int. Cl.⁴ .................... G01N 33/52; G01N 21/78
[52] U.S. Cl. ................................................. 356/446
[58] Field of Search ............... 356/39, 445, 446, 447, 356/448; 422/55, 57, 63, 65, 67

[56] References Cited

U.S. PATENT DOCUMENTS

| | | | |
|---|---|---|---|
| 3,907,503 | 9/1975 | Betts et al. | 356/446 |
| 3,980,437 | 9/1976 | Kishimoto et al. | 422/55 |
| 4,055,395 | 10/1977 | Honkawa et al. | 356/244 |
| 4,160,646 | 7/1979 | Furutani et al. | 356/448 |
| 4,268,173 | 5/1981 | Barnard et al. | 356/445 |

FOREIGN PATENT DOCUMENTS

| | | |
|---|---|---|
| 0056316 | 7/1982 | European Pat. Off. . |
| 0129203 | 12/1984 | European Pat. Off. . |
| 0129220 | 12/1984 | European Pat. Off. . |
| 3026436 | 2/1982 | Fed. Rep. of Germany ...... 356/446 |
| 3026439 | 2/1982 | Fed. Rep. of Germany . |
| 2462960 | 12/1983 | Fed. Rep. of Germany . |
| 2378277 | 8/1978 | France . |
| 2096314 | 10/1982 | United Kingdom ................ 356/445 |

Primary Examiner—R. A. Rosenberger
Attorney, Agent, or Firm—Theodore J. Leitereg

[57] ABSTRACT

A portable analyzer is disclosed. The analyzer comprises in combination a housing, an optical system comprising a light source, a detector, and one or more means for activating the optical system in generating a signal in response to a test element, means for manually moving the test element from a first position to a second position corresponding to a point of initiation of an operative condition of the optical system, means biasing the moving means toward said first position for controlling movement of the test element from the second position to the first position, means cooperative with said optical system, for processing the signal, and means, cooperative with the means for processing the signal, for displaying the processed signal.

23 Claims, 3 Drawing Sheets

PORTABLE ANALYZER

This is a continuation of pending application Ser. No. 675,485, filed Nov. 27, 1984, now abandoned incorporated herein by reference.

BACKGROUND OF THE INVENTION

1. Field of the Invention

Solid-phase reagents are easy to handle and, when introduced into optical analyzing systems, allow the performance of quantitative analyses. With development of various new measurement principles and new reagents, solid-phase reagents find wide use in the field of clinical examination such as confirmation of the appearance of a disease, the effect of a course of treatment, changes in the morbid state, etc. The solid-phase reagents generally are in the form of filter paper impregnated with a reagent (test paper) or in the form of a film made of a mixture of the reagent with a high molecular weight polymeric substance. The solid phase reagent is generally rigidly attached to a strip or a slide thereby forming an analyzing tool.

Analyzers which can efficiently analyze a plurality of test liquids and a plurality of solid-phase reagents in one operation have relatively large dimensions. Small portable analyzers generally measure only one item at a time. Such portable analyzers are frequently used for determining important data such as blood glucose, BUN, etc. These portable analyzers find wide use in hospitals, clinical laboratories, and the like.

In order to obtain reliable measurement data with regard to blood glucose or BUN, it is presently necessary either to measure one and the same component both in weak and high concentration or to measure a plurality of elements by sequentially measuring single items such as specific components of a test liquid. These specific components are determined by measuring a reaction element and a reference element with the use of a solid-phase reagent utilizing an immune chemical reaction. The conventional portable analyzers cannot perform in one operation the measurements required in such an approach.

For performing a plurality of measurement operations it is required either to provide a drive mechanism for feeding a plurality of test elements through a photometric unit of a sequential measurement device or to use a plurality of separate optical systems. In the latter case the overall dimensions of the device as well as the cost of the instrument are increased due to the larger number of elements in the optical system. Furthermore a measurement accuracy is reduced because of irregularity in characteristics between the elements. On the other hand, instruments which can carry out these functions are heavy because they require a motor as the drive means. Such instruments are not transportable because of their relatively large dimensions. They consume a relatively large amount of power for the motor supply. Furthermore such instruments cannot work continuously for a long period of time where batteries are used as a power source.

To utilize conventional small analyzers to perform their required functions requires repetition of measurements. Furthermore, the measurements are time consuming. Moreover, it is impossible to obtain correct measurement values because of variation of time periods from the beginning of a reaction to the time of measurement. Consequently, conventional portable analyzers cannot be used with an analyzing tool which carries several test elements.

2. Description of the Prior Art

The chemical analyzer for performing analysis on selective fluids is disclosed in U.S. Pat. No. 4,152,390. An analyzer apparatus and method of analyte detection are disclosed in U.S. Pat. No. 4,303,611. A cross slide table for microscopes is disclosed in U.S. Pat. No. 3,044,354. A cuvette assembly for use with photometric instrumentation and an analytical apparatus for use therewith are disclosed in U.S. Pat. No. 3,718,439. A digital glucose analyzer is disclosed in U.S. Pat. No. 3,920,969. A biochemical analysis apparatus is disclosed in U.S. Pat. No. 4,055,395. A method and apparatus for performing chemical analyses on selected fluids are disclosed in U.S. Pat. No. 4,257,862. An analyzer featuring loading and unloading means for a storage chamber and common drive means is disclosed in U.S. Pat. No. 4,424,191. A test system for the semi-automatic analyses of chemical constituents in a test fluid is disclosed in U.S. Pat. No. 3,907,503.

The Ames Division of Miles Laboratories, Incorporated, markets a urine analysis apparatus under the trademark Clinitek ® 10 and also markets a reflectance photometer under the trademark Seralyzer ®.

SUMMARY OF THE INVENTION

The analyzer of the invention comprises in combination a housing; an optical system comprising a light source, a detector, and one or more means for activating the optical system and generating a signal in response to a test element; means for manually moving the test element from a first position to a second position corresponding to a point of initiation of an operative condition of the optical system; means biasing the moving means toward the first position for controlling movement of the test element from the second position to the first position; means cooperative with the optical system, for processing the signal; and means, cooperative with the means for processing the signal, for displaying the process signal. The analyzer of the invention finds particular application in determining the amount of an analyte in a sample suspected of containing the analyte by the use of solid phase reagents.

DESCRIPTION OF THE SPECIFIC EMBODIMENTS

The analyzer of the present invention provides a number of advantages over conventional analyzers. These advantages include reduced power requirements, simple structure, light weight, ease of use, and the like. The advantages of the present invention are primarily realized from employment of the means for manually moving the test element from a first position to a second position corresponding to a point of initiation of an operative condition of the optical system and means biasing the moving means toward the first position for controlling movement of the test element from the second position to the first position.

The analyzer of the present invention will be described in greater detail with reference to the attached drawings.

Referring to FIG. 1 to FIG. 4, analyzer 10 comprises housing 12 which may be formed of any suitable light weight material such as, for example, plastic, and the like. Analyzer 10 further comprises an optical system comprising a light source 14, a detector 16, and one or more means for activating the optical system and generating a signal in response to a test element such as, for example, microswitch 18. Light source 14 is a conventional light source such as a light emitting diode and is monochromatic. Monochromatic light can be provided by a filtered-tungsten source with or without a fiber optic probe, filtered xenon strobe source, and the like. The optical system further comprises integrating sphere 20 which provides efficient collection of reflected light for greater sensitivity.

Figure 4:
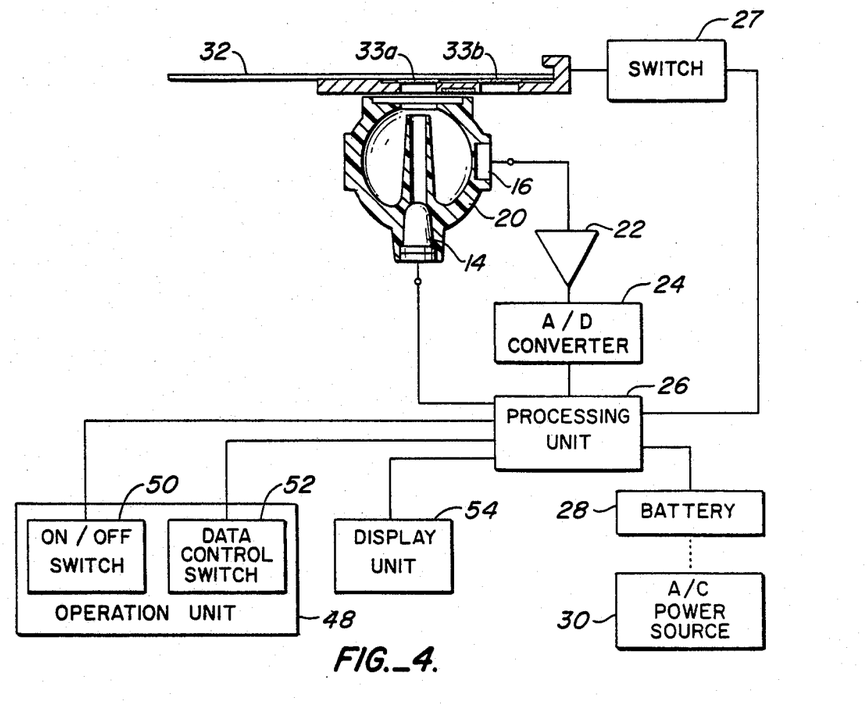
FIG. 4 is a block diagram showing treatment of signals in an apparatus in accordance with the present invention.

Referring to FIG. 4, detector 16 communicates with amplifier 22 which in turn communicates with A/D converter 24. Detector 16 communicates through 22 and 24 with processing unit 26, which can comprise, for example, a microcomputer for receiving an electric signal from the optical system, (2) synchronizing measurements, and (3) calculating measured values from quantities of electric signals and memorized control data. The optical system can be powered using, for example, batteries 28 or an A/C power source 30. The batteries may be self-charging batteries or batteries which may be charged from an A/C source. The measurement system can be activated by switch 27.

Reference is now made to FIGS. 2-5. Analyzer 10 further comprises means for manually moving an analyzing tool 31 (FIG. 5) from a first position to a second position corresponding to a point of initiation of an operative condition of the optical system. Such means includes holder 34 having slider 36 which moves in holder guides 38. Holder 34 also includes holder base 40 which is located on the upper part of the optical system. Holder 34 further includes a base 42 for supporting analyzing tool 31 and a cover 44 for confining analyzing tool 31 on base 42 in holder 34. Where the underside of cover 44 does not directly contact analyzing tool 31, pad 47 can be attached to the underside of cover 44 to provide intimate contact of such underside with 31.

Figure 2:
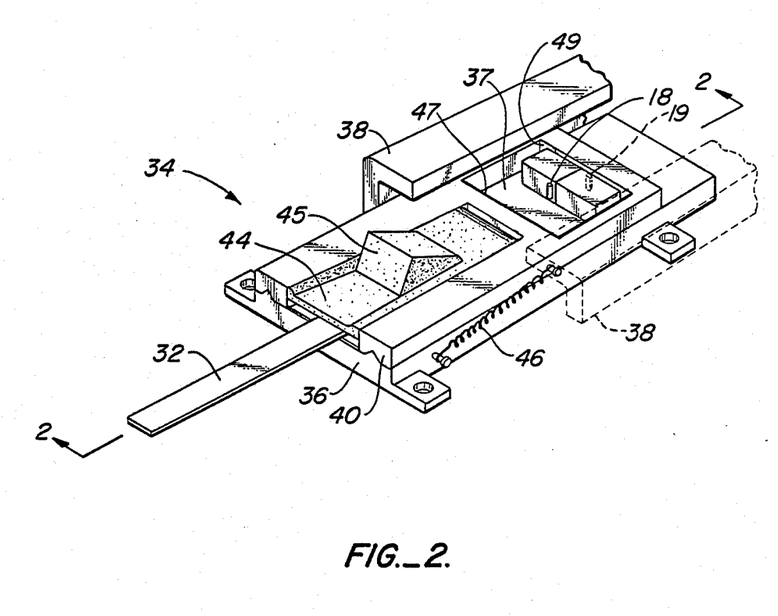
FIG. 2 is a perspective view of a mechanism for driving the holder for the analyzing tool of the analyzer of FIG. 1.
Figure 3:
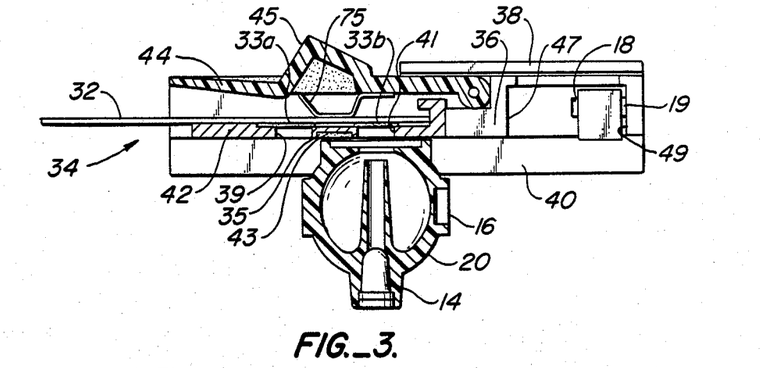
FIG. 3 is a longitudinal cross sectional view of the device of FIG. 1 with an optical system.

Slider 36 has an opening 37, preferably rectangular, with inner walls which include wall 47 and wall 49. The dimensions of opening 37 should be such as to provide appropriate activation and deactivation of the optical system of the present analyzer and permit sequential reading of the test elements and the analyzer reference element.

Holder 34 also includes apertures 39, 41, and 43, respectively, for allowing irradiation of the test elements and analyzer reference element and further allowing detection of the signal produced. The apertures are of a size sufficient to allow such irradiation of and detection of a signal from one of the elements and avoid irradiation of the other elements at that particular time.

Holder 34 further includes means biasing the moving means toward the first position for controlling movement of the test element from the second position to the first position. Referring to FIG. 2 this means can take the form, for example, of spring 46. Spring 46 is merely illustrative of types of biasing means in accordance with the present invention. In the embodiment illustrated in FIG. 2 the deformation energy of expanded spring 46 is used as a source for moving 36 from the second position to the first position in a controlled manner. However the deformation energy of a compressed spring can also be used for this purpose. Furthermore a band of rubber or other resilient material can be utilized in the present invention. The same purpose can be achieved with the use of a resilient mechanism such as a gas spring which is a sealed cylinder filled with gas or oil in which the spring constant is created due to compression energy of the gas or liquid. The number of springs and positions of their attachment can vary depending on the particular structure of the analyzer. In the case where resilient material is employed, holder 34 recoils after the quick return stroke and does not stop. A stopper can be used for stopping the return, or a damper can be utilized for absorbing the shock. This damper will stop the quick return motion of holder 34 under the action of spring 46 and assist in controlling the return of 36 from the second position to the first position.

Analyzer 10 further includes means, cooperative with the optical system, for processing the signal. As mentioned above this means includes amplifier 22 communicating with converter 24 which in turn communicates with central processing unit 26. Central processing unit 26 also communicates with operation unit 48 which includes a power on/off switch 50 and a data control switch 52.

Figure 1:
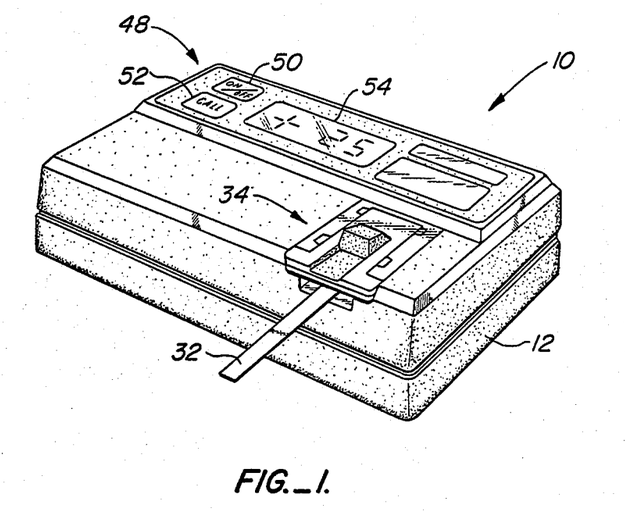
FIG. 1 is a perspective outer view of an analyzer in accordance with the present invention.

Analyzer 10 further includes means, cooperative with the means for processing the signal, for displaying the process signal. Referring to FIGS. 1 and 4 display unit 54 appears on the front face of analyzer 10. Display unit 54 communicates with central processing unit 26.

Figure 5:
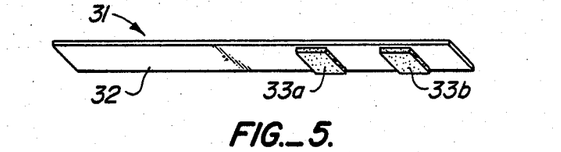
FIG. 5 is a perspective frontal view of an analyzing tool containing two test elements.

Reference is now made to FIG. 5. Analyzing tool 31 comprises support 32 having one or more assay test elements 33a and one or more reference test elements 33b. Test elements 33a and 33b are spaced apart from each other on support 32 to coincide with measurement apertures 39 and 41, respectively. The space between 33a and 33b generally corresponds to aperture 43 to allow irradiation of analyzer reference element 35 and the detection of a signal therefrom for calibration of the analyzer. In a preferred embodiment the test element contains reagents for producing a signal in relation to the amount of an analyte in the sample suspected of containing the analyte. More particularly the test element contains reagents of an immunochemical reaction. Examples of such test elements are found in U.S. patent application Ser. No. 374,849, filed May 4, 1982 and U.S. patent application Ser. No. 593,762, filed Mar. 27, 1984, the disclosures of which are incorporated herein by reference.

The assay test element includes at least a conjugate of a specific binding pair ("sbp") member and a label which provides an amount of a signal generating compound at the assay test element or measurement surface related to the amount of analyte in the assay medium. The reference test element or calibration surface is also present on the analyzing tool. The calibration surface provides a signal level from the signal generating compound as a result of at least one ligand-receptor binding involving an sbp member conjugated to a label where the sbp member associated with the calibration surface is different from the sbp member associated with the measurement surface. The ratio of the signal at the calibration surface to that at the measurement surface relates to the amount of analyte in a sample suspected of containing the analyte substantially independent of non-specific factors. The assay test element and the reference test element are therefore useful in a calibration assay method.

The above method provides for simultaneous calibration of the assay system during the performance of each individual test. The signal producing system as it relates to the production of a detectable signal at the two surfaces is subject to a number of the same conditions which affect the observed detectable signal. Thus, variations in the production of a detectable signal due to variations in conditions, endogenous materials in the sample, or the like, will affect the production of the detectable signal in parallel ways. The signal level of the calibration surface serves as a standard for the evaluation of the signal level of the measurement surface.

In one known method, an sbp member that differs from that associated with the measurement surface is employed on the calibration surface. The sbp member on the calibration surface binds to either the catalyst portion or to the sbp member portion of the catalyst-sbp member conjugate. The measurement surface includes the specific binding partner for the sbp member that forms part of the catalyst-mip conjugate. The production of the detectable product which produces the signal on the surface will be directly related to the amount of the catalyst which becomes bound to the measurement surface. By contrast, the amount of catalyst which binds to the calibration surface will not be solely dependent upon, and may be independent of, the amount of analyte in the medium.

Once the catalyst molecules are bound to the surfaces, the catalytic activity or turnover rate at the two surfaces will be subject to the same environment, so that the production of detectable product on the calibration surface can be used as a basis for a qualitative or quantitative determination of the concentration of analyte in the medium.

In another known method, the calibration surface includes a receptor that is capable of binding to the conjugate of the catalyst and the mip and is substantially incapable of binding to the catalyst or the sbp member apart from the conjugate. Such a receptor can be, e.g., a monoclonal antibody specific for the conjugate.

Before describing in detail the test elements and method or methods in which they are employed, a number of terms will be defined.

Definitions

Analyte—the compound or composition to be measured, which may be a ligand, which is mono- or polyepitopic, usually antigenic or haptenic, a single or plurality of compounds which share at least one common epitopic or determinant site, or a receptor.

The polyepitopic ligand analytes will normally be poly(amino acids), i.e., polypeptides and proteins, polysaccharides, nucleic acids, and combinations thereof. Such combinations include bacteria, viruses, chromosomes, genes, mitochondria, nuclei, cell membranes and the like.

The precise nature of the analytes together with numerous examples thereof are disclosed in U.S. Pat. No. 4,299,916 to Litman, et al., particularly columns 16 to 23, the disclosure of which is incorporated herein by reference.

Member of a specific binding pair ("sbp member")—one of two different molecules, having an area on the surface or in a cavity which specifically binds to a particular spatial and polar organization of the other molecule. The members of the specific binding pair are referred to as ligand and receptor (antiligand). These will usually be members of an immunological pair, although other specifically binding pairs such as biotin-avidin, hormones-hormone receptors, and the like are not immunological pairs. Homologous or complementary substances are ligand and receptor, while analogous substances are either ligands or receptors, which are differentiated in some manner, e.g., labeling.

Ligand—any organic compound for which a receptor naturally exists or can be prepared.

Receptor ("antiligand")—any compound or composition capable of recognizing a particular spatial and polar organization of a molecule, i.e., epitopic or determinant site. Illustrative receptors include naturally occurring receptors, e.g., thyroxine binding globulin, antibodies, enzymes, Fab fragments, lectins, nucleic acids and the like.

Ligand analog—a modified ligand which can compete with the analogous ligand for a receptor, the modification providing means to join a ligand analog to another molecule. The ligand analog will usually differ from the ligand by more than replacement of a hydrogen with a bond which links the ligand analog to a hub or label, but need not.

Poly(ligand analog)—a plurality of ligands or ligand analogs covalently joined together, normally to a hub nucleus. The hub nucleus is a polyfunctional material, normally polymeric, usually having a plurality of functional groups, e.g., hydroxy, amino, mercapto, ethylenic, etc., as sites for linking. The hub nucleus is normally water soluble or at least dispersible and will usually be at least about 35,000 daltons, but generally not exceeding about 600,000 daltons. Illustrative hub nuclei include polysaccharides, polypeptides, including proteins, nucleic acids, ion exchange resins and the like.

Surface ("test element")—the measurement surface ("assay test element") and calibration surface ("reference test element") will each be non-dispersed and have an available surface area of at least about 50 $\mu m^2$ and generally greater, often at least about 1 $mm^2$, usually being on a common support, particularly when less than about 0.5 $cm^2$, and may be of any material which is insoluble in water and provides the necessary properties for binding of an sbp member and a detectable signal generating compound to provide a desired signal level. Desirably, the surface will be gelatinous, permeable, bibulous, porous or have a rough or irregular structure, which may include channels or indentations, generally having a substantial void volume as compared to total volume. Depending upon the nature of the detectable signal generating compound, the surface will be adsorbent or non-adsorbent, preferably being weakly or non-adsorbent. The surface may be transparent or opaque, a single material or a plurality of materials, mixtures or laminates. A wide variety of materials and shapes may be employed. The surface will be capable of substantially retaining its integrity under the conditions of the assay, so that substances which are bound to the surface will remain bound to the surface and not diffuse into solution. It is desirable that underlying structures of both the measurement and calibration surfaces be substantially identical.

Catalyst-bound-sbp member—catalyst, usually an enzyme, conjugated to an sbp member. The catalyst is a member of the signal producing system and the mip is chosen to bind to the measurement surface in accordance with the particular protocol.

Signal-producing system--the signal-producing system includes at least one catalyst, usually at least one enzyme, and at least one substrate and may include two or more catalysts and a plurality of substrates, desirably including a combination of enzymes, where the substrate of one enzyme is the product of the other enzyme. The operation of the signal producing system is to produce a product which provides a detectable signal at the measurement surface related to the amount of catalyst bound to that surface, as a result of sbp member complex formation of the catalyst-bound-sbp member. The signal producing system, employed in whole or part at the calibration surface, also produces a detectable signal at the calibration surface. The level of the detectable signal is dependent on at least one factor independent of the amount of analyte. Other materials which may be included in the signal producing system include scavengers for an intermediate product, where a plurality of enzymes are employed.

The signal producing system provides for the production of a compound, which is normally the signal generating compound, but in some instances may react with another compound bound to the surfaces with the production, enhancement or destruction of the signal generating compound. While both enzymatic and non-enzymatic catalysts may be employed, usually there will be at least one enzyme catalyst employed in the signal producing system. In the event of there being only one catalyst, this catalyst will be conjugated to a mip for binding to the measurement surface through complex formation. In addition to the catalyst, there must be a solute which undergoes a transformation which results in a change in a detectable signal at the measurement surface.

For the most part, the product resulting from the transformation catalyzed by the catalyst-bound-sbp member will be the signal generating compound. Therefore, where there is only one catalyst, usually an enzyme, the signal producing system will involve the catalyst-bound-sbp member and its substrate.

Preferably, two catalysts will be employed, either a combination of an enzyme and a non-enzyme catalyst or two enzymes, where the two catalysts are related in that the product of one is the substrate of the other. In this system, there need be only one solute or substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the signal producing compound to provide the signal generating compound.

For the most part, the involved reactions will be hydrolysis or redox reactions. In the case of hydrolysis, substitution of a dye by a water solubilizing compound joined by an enzymatically labile bond, where two enzymatic steps are required to result in the insoluble dye product, is illustrative of this type of system. By contrast, in redox reactions, the first enzyme can produce an essential substrate for the second enzyme, where the second enzyme catalyzes the reaction between the product of the first enzyme and the dye precursor.

The enzymatic reaction may involve modifying the solute to a product which is the substrate of another enzyme or production of a compound which does not include a substantial portion of the solute, which serves as an enzyme substrate. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with the signal generator precursor to produce the signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued July 10, 1979, the appropriate portions of which are incorporated herein by reference.

Various combinations of enzymes may be employed to provide a signal generating compound at the surface. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound. The following table is illustrative of various combinations which may be employed to provide for preferential production of the signal generating compound at the surface. Usually there will be a preferred catalyst at the surface, since as indicated previously, by appropriate choice of the catalyst at the surface, a greater number of reagents may be combined in a single formulation.

For a more detailed discussion of the signal producing system and illustrative examples, see U.S. Ser. No. 374,849, filed May 4, 1982.

Ancillary Materials—Various ancillary materials will frequently be employed in the calibration assays. Particularly, enzyme substrates, cofactors, activators, scavengers, inhibitors or the like may be included in the assay medium.

In addition, buffers will normally be present, as well as stabilizers. Frequently in addition to these additives, additional proteins may be included, such as albumins; or surfactants, particularly non-ionic surfactants, e.g., polyalkylene glycols, or the like.

The underlying surface of the test elements can vary widely. Generally, the underlying surface will be the same for both the calibration and the measurement surfaces. Normally, the surface is chosen so as not to be strongly absorbent for members of the signal producing system to minimize interference with the assay. The underlying structure of the surface may take different forms, have different compositions and may be a mixture of compositions or laminates or combinations thereof. The material chosen for the surface must be able to interact with the signal generating compound by desolubilization of the signal generating compound or complexation reaction or interaction of another compound bonded to the surface, so as to form, destroy or interact with the signal generating compound.

The surface may assume a variety of shapes and forms and may have varied dimensions, depending on the manner of use and measurement. Illustrative surfaces may be pads or discs, which may be flat, concave or convex. The thickness is not critical, generally being from about 0.1 to 2 mm thick and of any convenient diameter or other dimensions. Typically, the calibration surface and the measurement surface will be supported on test element support 32 which can be for example, a strip, to form analyzing tool 31. The surface may form an integral part of the support or be distinct from the support, typically forming an applied layer on the support or spaced apart from the support and supported by two or more spacers (see, for example, FIG. 5).

The surface will typically be porous, with various pore sizes employed, depending on the nature of the system. The surface may be polyfunctional or be capable of being polyfunctionalized, so as to permit covalent bonding of sbp members, as well as to permit bonding of other compounds which form a part of the signal producing system. The precise nature of the surface is discussed in detail in U.S. Pat. No. 4,299,916 to Litman, et al., incorporated herein by reference.

Binding of sbp members to the surface material to form the measurement and calibration surfaces may be by well-known techniques, commonly available in the literature. See, for example, "Immobilized Enzymes," Ichiro Chibata, Halsted Press, N.Y. (1978) and Cuatrecasas, *J. Bio. Chem.*, 245:3059 (1970).

A wide variety of organic and inorganic polymers, both natural and synthetic, and combinations thereof, may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials which may be employed include paper, glasses, ceramics, metals, metaloids, semi-conductive materials, cermets, silicates or the like. In addition are included substrates that form gels, such as proteins, e.g., gelatins, lipopolysccharides, silicates, agarose; and polyacrylamides or polymers which form several aqueous phases, such as dextrans, polyalkylene glycols (alkylene of 2 to 3 carbon atoms) or surfactants, e.g., amphiphilic compounds, such as phospholipids, long chain (12-24 carbon atoms) alkyl ammonium salts and the like.

The simultaneous calibration assay is carried out by placing the portion of analyzing tool 31 containing the test elements in an aqueous zone or medium, where the final assay medium may be the result of prior individual additions of reagents or combinations of reagents and incubations, prior separations involving removal of surfaces from an aqueous medium and transfer to a different aqueous medium having one or more reagents, or combinations thereof. While the assay method does not require a separation of labeled conjugate which is unbound from that which is bound to one or both surfaces through sbp member complexes, in many protocols a developer solution will be employed which is substantially free of unbound catalyst. The various media involved in the assay consist of a liquid phase and a solid phase which defines both the measurement and calibration "surfaces."

In carrying out the assay, the test elements will be contacted by the sample, and by the members of the signal producing system, and any ancillary materials, in an aqueous medium, either concurrently or stepwise, to provide a detectable signal associated with the test elements. The detectable signal at the measurement surface will be related to the amount of the labeled conjugate bound to that surface, which relates to the amount of analyte in the sample. Depending upon the nature of the signal producing system and the desired method for detecting the signal, the surfaces may be read in the assay medium or will be read separate from the assay medium.

In carrying out the assay, an aqueous medium will normally be employed. Other polar solvents may also be included, usually oxygenated organic solvents of from 1-6, more usually from 1-4 carbon atoms, including alcohols, ethers and the like. Usually these cosolvents will be present in less than about 40 weight percent, more usually in less than about 20 weight percent.

The pH for the medium will usually be in the range of about 4-11, more usually in the range of about 5-10, and preferably in the range of about 6.5-9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, tris, barbital and the like. The particular buffer employed is not critical to this invention but in individual assays, one buffer may be preferred over another.

Moderate temperatures are normally employed for carrying out the assay. Constant temperatures during the period of the measurement are generally not required, but rapid and large fluctuations are not desirable. The temperatures for the determination will generally range from about 10°-50° C., more usually from about 15°-45° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique and the concentration of the analyte of interest will normally determine the concentration of the other reagents.

The concentration of various reagents will vary widely depending upon which protocols are employed, the nature of the analyte, the sbp members which is bound to the surface and the sbp members which is bound to the catalyst, the required sensitivity of the assay, and the like. In some instances, large excesses of one or the other of the sbp members may be employed, while in some protocols the sensitivity of the assay will be responsive to variations in the sbp members ratios.

The common support for the test elements is conveniently a rod or plastic film as used in immunochemical strips. The precise nature and dimensions of such strips are not critical and may be chosen to conform with the dimensions of holder 34. It is desirable that both test elements be placed at one end of an elongate strip to form the analyzing tool so that they may be easily immersed in a relatively small sample, typically 100 μl to 2 ml. Mounting the surfaces adjacent each other also facilitates use of the portable analyzer of the invention. The surfaces may be vertically or horizontally positioned.

As already indicated, more than two surfaces may be employed, involving either or both a plurality of assay test elements or measurement surfaces and a plurality of reference test elements or calibration surfaces.

A wide variety of protocols may be involved, where one or more solutions will be employed. Contact with the solutions may involve agitation or standing. Incubation steps may be involved, generally varying from about 0.5 minutes to 1 hour, more usually from about 2 minutes to 30 minutes. Depending upon the various protocols: (1) all of the materials involved in the assay may be combined with the sample; (2) the catalyst reagent may be combined with the sample, while one or more substrates are combined in a separate solution, referred to as the developer solution, where the test elements are transferred from solution to solution; or (3) the sample, catalyst reagent and at least a portion of the substrates combined in one solution, while the remaining substrates combined in another solution, where the test elements are transferred from solution to solution. Normally, wash steps are not required between transfers since little interference is observed as a result of any adventitious non-specific binding. Competitive and non-competitive protocols may be employed.

In the simplest protocol, one would have all the reagents combined in an appropriate formulation, conveniently a lyophilized powder formulation, which is dissolved in a measured amount of an aqueous medium containing the sample. After a sufficient time for the solution to become homogeneous, the test elements may be introduced into the sample solution, where the signal producing system involves two enzymes, related by one enzyme producing a product which is the substrate of the other enzyme. By having the first enzyme bound to both the measuring surface and the calibration surface, one can combine the second enzyme with the substrate for the first enzyme without concern about premature reaction, since until the first enzyme produces the necessary substrate for the second enzyme, there will be no reaction. Where only a single catalyst is employed in the signal producing system, it will normally be necessary to have at least two solutions with separate contacting of the test elements with the two solutions, one of the solutions having the substrate for the catalyst and the other solution having the catalyst-bound-sbp members.

The signal generating compound may provide an increase or decrease in the observed signal. The signal generating compound will preferentially bind to the test elements and provide a detectable signal, which is detected by dector 18. The signal generating compound will normally be substantially insoluble in the medium in which it is produced and will be derived either directly or indirectly from a catalytic product.

In a number of situations, a scavenger may be desirable. Alternatively, an enzyme inhibitor may be employed, which selectively deactivates the enzyme in solution but is substantially inactive toward the enzyme bound to the surface.

For quantitation, a ratio of signal level on the measurement surface as related to the signal level on the calibration surface is developed. Thus, by providing for a particular time period from the initiation of production of a signal generating compound to termination of further production of the signal generating compound, the ratio of the signal from the measurement surface and calibration surface can be related to standard values for quantitating the amount of analyte. The time is not a critical factor, so long as a sufficient change in signal occurs at both the measurement surface and calibration surface, but not so long that a change in signal can no longer be observed at the surfaces. Thus, the ratio will provide a result which is relatively insensitive to time, temperature and endogenous interference.

For a description of various methods in which the portable analyzer of the subject invention can be used, see U.S. Ser. No. 374,849, filed May. 4, 1982, and U.S. Pat. No. 4,299,916, cols. 7-16, which subject matter is incorporated herein by reference.

The operation of analyzer 10 will now be described in detail with reference to the attached drawings. The assay test element and reference test element on test element support 32 will have previously been employed in an assay method such as that described above. The test element should be analyzed within about 10 to 120 sec from the end of the test reaction. Analyzing tool 31 is placed in holder 34 by lifting cover 44 and placing support 32 onto base 42 and then placing cover 44 over element 32. Analyzing tool 31 is placed on base 42 with test elements 33 facing in the direction of the optical system. Knob 45 is engaged with a finger to overcome the restoring force of spring 46 and holder 34 is pushed in the direction of microswitch 18 until wall 47 of opening 37 in holder 34 engages microswitch 18. The engagement of microswitch 18 activates the optical system and light source 14 and assay test element 33a is measured. When the finger is released from knob 45 holder 34 begins its return to the first position under the effect of the restoring force of spring 46. During this return from the second position to the first position standard analyzer reference element or reflection sample 35 is measured. Upon the return of holder 34 to its initial position wall 49 of opening 37 in holder 34 engages microswitch 19 which causes light source 14 after a certain predetermined period of time to turn off. During the period of time between the engagement of microswitch 19 by surface 49 and the actual deactivation of light source 14, reference test element 33b is measured.

The optical output signals from the irradiated test elements and analyzer reference element are detected by detector 16 and sequentially converted by converter 22 and fed into central processing unit 26 through unit 24. A value is then displayed on display unit 54. This value can be related to the presence or absence of analyte in the sample.

Figure 6:
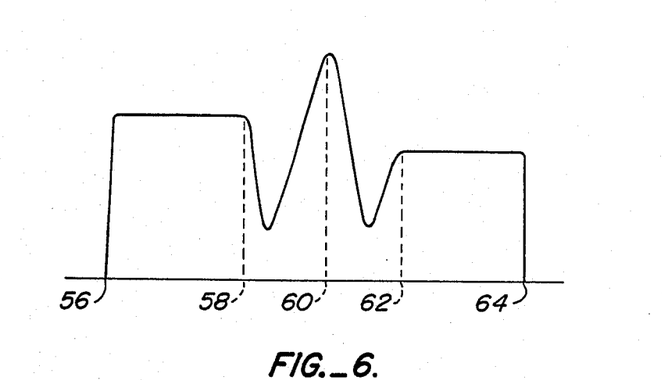
FIG. 6 is a graphic depiction of the mode of reception of signal from two tests elements and an analyzer reference element.

The manner in which the signals are received from irradiated test elements 33 and analyzer reference element 35 will be explained in greater detail with reference to FIG. 2 to FIG. 6. When holder 34 is pushed to FIG. 2 to the position of engagement of microswitch 18, the optical system is activated which includes activation of light source 14. This initiation of the operative condition of the optical system is indicated by the numeral 56 in FIG. 6. When the finger is released from knob 45, represented by the numeral 58 in FIG. 6, holder 34 begins its return to the initial position under the restorative force of spring 46. Microswitch 19 is engaged when holder 34 returns to the first position, and a signal is transmitted to light source 14 which, after a certain predetermined period of time, is turned off. From condition 56 to condition 58 holder 34 does not move. A signal received during this period of time comprises a measured value which corresponds to test element 33a, that is to the assay test element. Condition 60 in FIG. 6 corresponds to the maximum quantity of the reflected light received from standard reflection element 35 during the return of holder 34 from the second position to the first position. Condition 62 is the point at which holder 34 returns to the initial position and microswitch 19 is engaged. In a predetermined period of time after this engagement, light source 14 is turned off, which is represented in FIG. 6 at condition 64. Holder 34 moves during the period between conditions 58 and 62. A signal generated in the period between conditions 62 and 64, i.e., the signal from the moment when holder 34 stops to the moment when light source 14 is switched off, represents the measured value of reference test element 33b.

The three measured values obtained after treatment of the signals in central processing unit 26 are used for determining percents of reflection from each of the irradiated elements, i.e., from reference test element 33b and assay test element 33a. The quantity of the light reflected from the standard reflection element 35 is taken as 100%. In this manner the reflection from each of the test elements is compared and then related to one another.

As mentioned above the results of the measurements obtained in the above manner are shown on display 54. The displayed values can be set to be automatically extinguished after a certain period of time. Prior to being extinguished from the display, the measurements can be memorized in central processing unit 26. If necessary these measurements can be called back by means of data call keys 52 or sent to another printer, data storage, or any other external device.

To perform a measurement on a subsequent analyzing tool, the previous analyzing tool is removed from the analyzer and the new analyzing tool is placed therein. The above-described steps are then repeated.

Figure 7A:
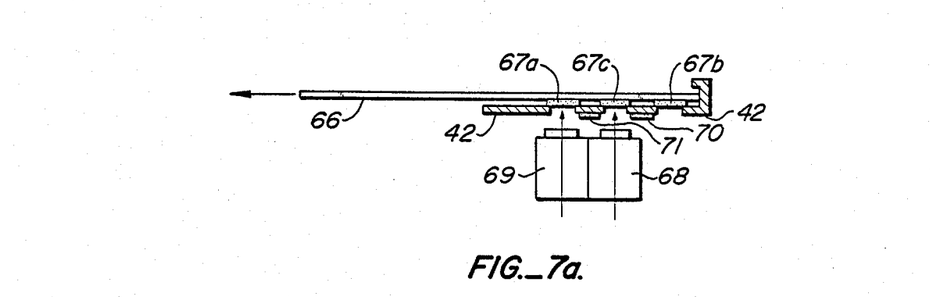
FIGS. 7a and 7b depict a configuration of the apparatus of the present invention for analyzing an analyzing tool containing three test elements.
Figure 7B:
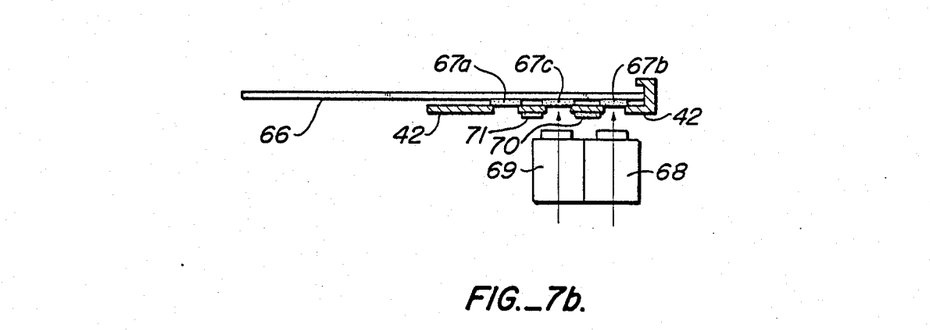
Figure 8:
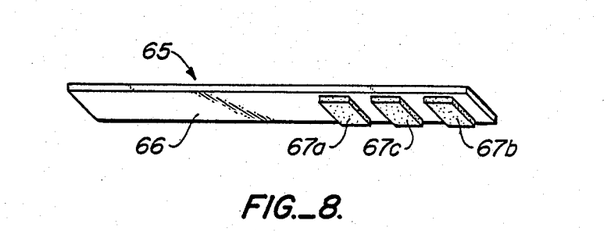
FIG. 8 is a perspective frontal view of an analyzing tool containing three test elements.

The operation of the analyzer of the invention will be next described in its application to the measurement of three test elements. Referring to FIG. 8, test element support 66 has assay test elements 67a and 67b and reference test element 67c. Referring now to FIG. 7 analyzing tool 65 comprising test element support 66, after being utilized in a method such as that described above, is placed on the base 42 of holder 34. Two optical systems are employed, which systems are designated in FIGS. 7a and 7b as 68 and 69. The optical systems employ a light source, e.g., and LED and two detectors which also serve to collect the emitted light. Analyzer reference elements 70 and 71 are also included in holder 34.

In operation, holder 34 is moved from the first position to the second position wherein microswitch 18 and optical systems 68 and 69 are activated. Assay reference element 67c and assay test element 67a are irradiated and measured. This condition is depicted in FIG. 7a. After knob 45 is released holder 34 begins its return under the restraining force of spring 46 to its initial or first position. During the return analyzer reference elements 70 and 71 are respectively irradiated and measured by optical system 68 and 69. Upon the return of holder 34 to the initial position, microswitch 19 is activated and assay test element 67b is irradiated and measured by optical system 68 and assay reference element 67c is irradiated and measured by optical system 69. The signals obtained from the above measurements are processed and displayed as described above.

The above description is provided by way of illustration and not to be a limitation. For example, instead of reflected light the measuring system can be based on fluorescent light depending upon the signal producing system employed in the assay.

In the embodiments illustrated above, measurements are carried out where the test elements on the test element support are in stationary positions and the analyzer reference element is movable. It is possible, however, to perform measurements in both measurement positions when all measured elements are stationary, or when all of them are movable. The number of measurement points is also unlimited and any number of dynamic and static measurements can be combined as required. However it is recommended that no more than two stationary measurement positions be used. Moreover, various modes of synchronization can be applied to signals received during the stationary and dynamic periods of the irradiation and measurement cycle. For example, by central processing unit 26 only flat portions of signals from detector 16 can be registered or only maximum points of signals from detector 16 can be received. Moreover, a photo coupler may be used as a synchronizing element.

Various modifications in the structure or materials of the device are possible. For example, a separate key can be provided, apart from microswitches associated with the movement of holder 34, for the power source for the optical system. This separate key may be interlocked with main switch 50 shown in the drawings, or it may have an additional function. Microswitches can be used only for switching the light source on, and the latter can be extinguished automatically in a predetermined period of time. The analyzer reference element can be attached to the bottom surface of cover 44 rather than being attached to holder base 42.

As indicated above, the present invention derives its benefits primarily from the feature of having (1) means for manually moving the test element from a first position to a second position corresponding to a point of initiation of an operative condition of the optical system and (2) means biasing the moving means toward the first position for controlling movement of the test element from the second position to the first position. Thus the invention makes it possible to produce a light weight, small, and portable analyzer which, contrary to conventional analyzers of this type, allows measurement of a plurality of test elements. Even with a plurality of test elements, all the elements can be measured in one simple operation, i.e., pushing the holder knob with a finger. Therefore, problems associated with an increased number of test elements are eliminated. The test elements and the analyzer reference element are measured almost simultaneously.

Although the foregoing invention has been described in some detail by way of illustration and example for the purposes of clarity and understanding, it will be obvious that certain changes or modifications may be practiced within the scope of the appended claims.

What is claimed is:

1. An analyzer comprising in combination
   a housing
   an optical system comprising a light source, a detector, and one or more means for activating said optical system and generating a signal in response one or more test elements on a support, means for manually moving said support from a first position to a second position corresponding to a point of initiation of an operative condition of said optical system, means biasing said moving means toward said first position for controlling movement of said moving means from said second position to said first position to a point of termination of said operative condition of said optical system, whereby a signal is generated for each test element during said operative condition, means, cooperative with said optical system, for processing said signal, and means, cooperative with said means for processing said signal, for displaying the processed signal.

2. The analyzer of claim 1 wherein said optical system is responsive to a test element which is part of an analyzing tool comprising one or more assay test elements and one or more reference test elements.

3. The analyzer of claim 1 wherein said optical system is responsive to a test element containing reagents of an immunochemical reaction.

4. The analyzer of claim 1 wherein said optical system is responsive to a test element containing reagents for producing a signal in relation to the amount of an analyte in a sample suspected of containing the analyte.

5. The analyzer of claim 1 wherein the means for manually moving the test element includes a holder for the test element.

6. The analyzer of claim 5 wherein the holder contains an aperture in a position corresponding to the position of the test element when the test element is placed in the holder.

7. The analyzer of claim 5 wherein the holder is separable from the analyzer.

8. The analyzer of claim 5 wherein said holder comprises a base for supporting said test element, a cover for said test element, and guide means for slidable movement of said holder in said analyzer.

9. The analyzer of claim 1 wherein said biasing means is a resilient material.

10. The analyzer of claim 1 wherein said biasing means is a spring.

11. The analyzer of claim 1 wherein said biasing means is a gas spring.

12. The analyzer of claim 1 wherein said biasing means includes a damper.

13. The analyzer of claim 1 wherein said means for processing said signal includes a microprocessor.

14. A portable analyzer comprising in combination a housing an optical system comprising a light source, a detector, and one or more means for activating said optical system and generating a signal in response to one or more test elements on a support, a holder for said support comprising a base for supporting said support and a cover, guide means incorporated into said housing for slidable movement of said holder within said analyzer, said holder being capable of manual movement in said analyzer from a first position to a second position corresponding to a point of initiation of an operative condition of said optical system by the interaction of said moving means and first switching means, bias means for controlling the return of said holder from said second position to said first position to a point of termination of said operative condition of said optical system by interaction of said moving means and second switching means, whereby a signal is generated for each test element during said operative condition, means, cooperative with said optical system, for processing said signal, and means, cooperative with said means for processing said signal, for displaying the processed signal.

15. The analyzer of claim 14 wherein the optical system is responsive to a test element which is part of an analyzing tool comprising one or more assay test elements and one or more reference test elements.

16. The analyzer of claim 14 wherein the optical system is responsive to a test element containing reagents of an immunochemical reaction.

17. The analyzer of claim 14 wherein the optical system is responsive to a test element containing reagents for producing a signal in relation to the amount of analyte in a sample suspected of containing the analyte.

18. The analyzer of claim 14 wherein said holder contains an aperture in a position corresponding to the position of the test element when the test element is placed in the holder.

19. The analyzer of claim 14 wherein the holder is separable from said analyzer and adapted for use with said analyzer.

20. The analyzer of claim 14 wherein said bias means is a resilient material.

21. The analyzer of claim 14 wherein said bias means is a spring.

22. The analyzer of claim 14 wherein said bias means is a gas spring.

23. The analyzer of claim 14 which further includes an analyzer reference element on said support.

* * * * *